(12) United States Patent
Saito et al.

(10) Patent No.: US 11,287,602 B2
(45) Date of Patent: Mar. 29, 2022

(54) OPTICAL UNIT AND ENDOSCOPE

(71) Applicant: OLYMPUS CORPORATION, Tokyo (JP)

(72) Inventors: Kanako Saito, Koganei (JP); Takeshi Saito, Koganei (JP)

(73) Assignee: OLYMPUS CORPORATION, Tokyo (JP)

(*) Notice: Subject to any disclaimer, the term of this patent is extended or adjusted under 35 U.S.C. 154(b) by 223 days.

(21) Appl. No.: 16/710,207

(22) Filed: Dec. 11, 2019

(65) Prior Publication Data

US 2020/0116974 A1  Apr. 16, 2020

Related U.S. Application Data

(63) Continuation of application No. PCT/JP2017/021802, filed on Jun. 13, 2017.

(51) Int. Cl.
| | |
|---|---|
| *G02B 7/04* | (2021.01) |
| *G02B 23/24* | (2006.01) |
| *A61B 1/00* | (2006.01) |

(52) U.S. Cl.
CPC ............ *G02B 7/04* (2013.01); *A61B 1/00188* (2013.01); *G02B 23/243* (2013.01); *G02B 23/2438* (2013.01)

(58) Field of Classification Search
CPC ........ G02B 7/04–7/105; G02B 23/2423–2438; G02B 23/2476; H02K 41/0356–41/0354; G11B 7/095–7/0937; A61B 1/00188
(Continued)

(56) References Cited

U.S. PATENT DOCUMENTS

| | | | | |
|---|---|---|---|---|
| 4,864,170 A | * | 9/1989 | Eguchi | G11B 7/08582 310/12.04 |
| 7,064,912 B2 | * | 6/2006 | Yamamoto | G02B 7/023 359/824 |

(Continued)

FOREIGN PATENT DOCUMENTS

| | | |
|---|---|---|
| CN | 106170054 A | 11/2016 |
| CN | 106233181 A | 12/2016 |

(Continued)

OTHER PUBLICATIONS

International Search Report dated Sep. 19, 2017 received in PCT/JP2017/021802.

*Primary Examiner* — Zachary W Wilkes
(74) *Attorney, Agent, or Firm* — Scully, Scott, Murphy & Presser, P.C.

(57) ABSTRACT

An optical unit includes: a moving frame disposed so as to freely move back and forth inside a fixed barrel and configured to hold a moving lens; an actuator configured to drive the moving frame along an optical axis of the moving lens; a plurality of spherical bodies configured to make the moving frame slidable; a plurality of guide grooves configured to guide the plurality of spherical bodies; a plurality of magnets disposed so as to generate magnetic force in a direction orthogonal to the optical axis; and a magnetic member disposed at a facing position of the plurality of magnets, and configured to cancel attractive forces in opposing directions generated with the plurality of magnets by the magnetic force and generate urging force only in a direction of bringing the plurality of spherical bodies into contact with the guide grooves at the moving frame.

20 Claims, 10 Drawing Sheets

(58) Field of Classification Search
USPC ........................................................ 359/824
See application file for complete search history.

(56) References Cited

U.S. PATENT DOCUMENTS

| | | | | |
|---|---|---|---|---|
| 7,376,962 | B2* | 5/2008 | Kimura | G11B 7/0935 |
| | | | | 369/44.15 |
| 7,656,596 | B2* | 2/2010 | Matsumoto | G02B 7/10 |
| | | | | 359/826 |
| 7,715,124 | B2* | 5/2010 | Ito | G02B 7/023 |
| | | | | 359/814 |
| 8,027,106 | B2* | 9/2011 | Kim | G02B 7/102 |
| | | | | 359/824 |
| 9,420,183 | B2* | 8/2016 | Hwang | H02K 41/0356 |
| 9,438,801 | B2* | 9/2016 | Hwang | H04N 5/2254 |
| 9,549,109 | B2* | 1/2017 | Kim | G02B 7/006 |
| 9,891,407 | B2* | 2/2018 | Baek | G03B 3/10 |
| 9,924,854 | B2* | 3/2018 | Iwasaki | A61B 1/00188 |
| 9,958,756 | B2* | 5/2018 | Hu | G03B 5/00 |
| 10,054,759 | B2* | 8/2018 | Kang | G02B 27/646 |
| 10,422,974 | B2* | 9/2019 | Kim | G03B 5/04 |
| 11,029,480 | B2* | 6/2021 | Kawanabe | H04N 5/2254 |
| 2008/0272869 | A1* | 11/2008 | Takayama | A61B 1/00188 |
| | | | | 335/219 |
| 2009/0180202 | A1* | 7/2009 | Knoedgen | G02B 7/023 |
| | | | | 359/824 |
| 2015/0160470 | A1* | 6/2015 | Terajima | G02B 7/08 |
| | | | | 359/557 |
| 2016/0241787 | A1* | 8/2016 | Sekimoto | G02B 7/08 |
| 2016/0342069 | A1 | 11/2016 | Inoue | |
| 2017/0065157 | A1 | 3/2017 | Iwasaki et al. | |
| 2017/0235095 | A1* | 8/2017 | Sekimoto | G02B 27/646 |
| | | | | 359/824 |
| 2018/0003920 | A1* | 1/2018 | Hu | G02B 7/10 |
| 2018/0292641 | A1* | 10/2018 | Ito | G02B 23/2476 |
| 2019/0265432 | A1* | 8/2019 | Kawanabe | G02B 7/003 |
| 2019/0271825 | A1* | 9/2019 | Kawanabe | G02B 7/02 |
| 2020/0116974 | A1* | 4/2020 | Saito | G02B 23/243 |

FOREIGN PATENT DOCUMENTS

| | | |
|---|---|---|
| JP | H08-29656 A | 2/1996 |
| JP | 2008-040188 A | 2/2008 |
| JP | 2015-141389 A | 8/2015 |
| KR | 20140030767 A * | 3/2014 |
| KR | 2015-0124036 A | 11/2015 |
| WO | 2016/132883 A1 | 8/2016 |

* cited by examiner

OPTICAL UNIT AND ENDOSCOPE

CROSS REFERENCE TO RELATED APPLICATION

This application is a continuation application of PCT/JP2017/021802 filed on Jun. 13, 2017, the entire contents of which are incorporated herein by this reference.

BACKGROUND OF INVENTION

1. Field of the Invention

The present invention relates to an optical unit including a moving lens frame and an endoscope including the optical unit.

2. Description of the Related Art

In recent years, an endoscope capable of observing a site to be examined, which cannot be directly viewed, by inserting an elongated insertion portion into a body cavity or the like has been widely used. As such an endoscope, an electronic endoscope provided with an image pickup apparatus as an optical unit is known.

In addition, for an image pickup apparatus including a zoom function and a focus function of a camera or the like, a configuration of sliding a moving lens frame that holds a moving lens by a guide shaft that guides rectilinearly and a sleeve is well-known.

In this way, when using the guide shaft and the sleeve or the like, since a frictional coefficient of sliding friction is high, grease or oil is used to reduce the frictional coefficient. Note that when driving force of an actuator that drives a moving lens frame adopted to a digital single lens reflex camera or the like is large, it is not a problem even if the oil or the grease that generates viscosity resistance is used.

However, for an especially small-sized image pickup apparatus mounted on a cellular phone, an endoscope or the like, since the actuator that drives the moving lens frame is also small-sized, it is necessary to drive the moving lens frame even with the small driving force by the actuator.

Therefore, when an image pickup apparatus is configured using a guide shaft and a sleeve, the viscosity resistance due to grease and oil to the small driving force of an actuator becomes a problem. Thus, it has been difficult to miniaturize the image pickup apparatus including a moving lens frame of a configuration using a shaft and a sleeve, and adoption to a cellular phone and an endoscope has been difficult.

Then, in order to drive a moving lens frame even with a driving force of a small-sized actuator, for example, an invention of an image pickup apparatus including an optical unit adopting ball sliding by rolling friction as disclosed in Japanese Patent Application Laid-Open Publication No. 8-29656 or Japanese Patent Application Laid-Open Publication No. 2008-40188 has been proposed.

SUMMARY OF THE INVENTION

An optical unit in one aspect of the present invention includes: a moving frame disposed so as to freely move back and forth inside a fixed barrel and configured to hold a moving lens; an actuator configured to drive the moving frame along an optical axis of the moving lens; a plurality of spherical bodies configured to make the moving frame slidable with respect to the fixed barrel in a direction along the optical axis; a plurality of guide grooves configured to guide sliding of the plurality of spherical bodies along the optical axis; a plurality of magnets disposed at point symmetrical positions around the optical axis; and a plurality of magnetic members disposed at facing positions of the plurality of magnets.

For an endoscope in one aspect of the present invention, an optical unit including: a moving frame disposed so as to freely move back and forth inside a fixed barrel and configured to hold a moving lens; an actuator configured to drive the moving frame along an optical axis of the moving lens; a plurality of spherical bodies configured to make the moving frame slidable with respect to the fixed barrel in a direction along the optical axis; a plurality of guide grooves configured to guide sliding of the plurality of spherical bodies along the optical axis; a plurality of magnets disposed at point symmetrical positions around the optical axis; and a plurality of magnetic members disposed at facing positions of the plurality of magnets is disposed at a distal end portion of an insertion portion.

An optical unit in another aspect of the present invention includes: a moving frame disposed so as to freely move back and forth inside a fixed barrel and configured to hold a moving lens; an actuator configured to drive the moving frame along an optical axis of the moving lens; a plurality of spherical bodies configured to make the moving frame slidable with respect to the fixed barrel in a direction along the optical axis; a plurality of guide grooves configured to guide sliding of the plurality of spherical bodies along the optical axis; a plurality of magnets disposed so as to generate magnetic force in a direction orthogonal to the optical axis; and a plurality of magnetic members disposed at facing positions of the plurality of magnets, and configured to cancel attractive force in an opposite direction generated among the plurality of magnets by the magnetic force and generate urging force only in a constant direction of bringing the plurality of spherical bodies into contact with the guide grooves at the moving frame.

For an endoscope in another aspect of the present invention, an optical unit including: a moving frame disposed so as to freely move back and forth inside a fixed barrel and configured to hold a moving lens; an actuator configured to drive the moving frame along an optical axis of the moving lens; a plurality of spherical bodies configured to make the moving frame slidable with respect to the fixed barrel in a direction along the optical axis; a plurality of guide grooves configured to guide sliding of the plurality of spherical bodies along the optical axis; a plurality of magnets disposed so as to generate magnetic force in a direction orthogonal to the optical axis; and a plurality of magnetic members disposed at facing positions of the plurality of magnets, and configured to cancel attractive force in an opposite direction generated among the plurality of magnets by the magnetic force and generate urging force only in a constant direction of bringing the plurality of spherical bodies into contact with the guide grooves at the moving frame is disposed at a distal end portion of an insertion portion.

DETAILED DESCRIPTION OF THE PREFERRED EMBODIMENT

Hereinafter, the embodiment of the present invention will be described with reference to the drawings.

Figure 1:
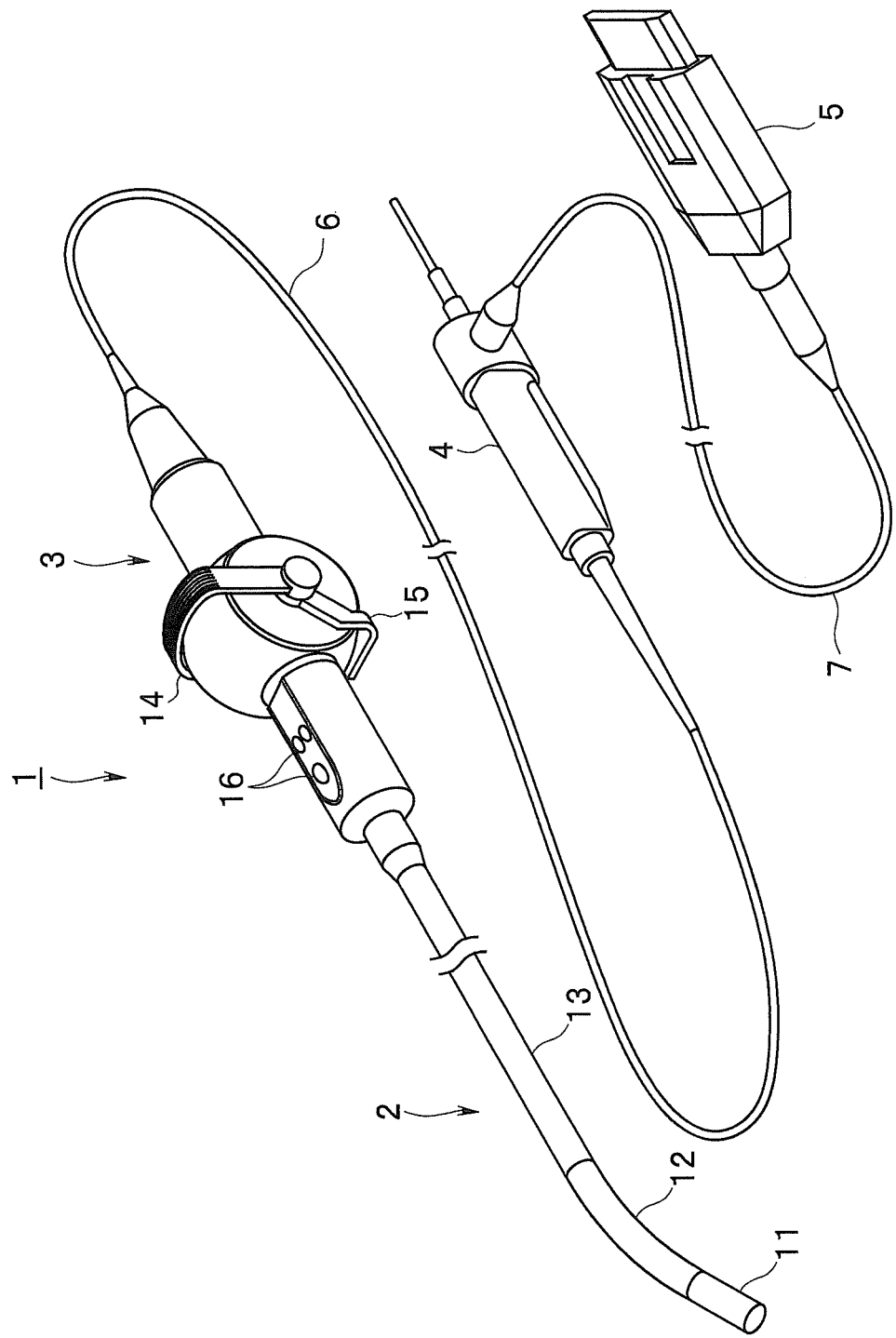
FIG. 1 is a perspective view illustrating a configuration of an endoscope.
Figure 2:
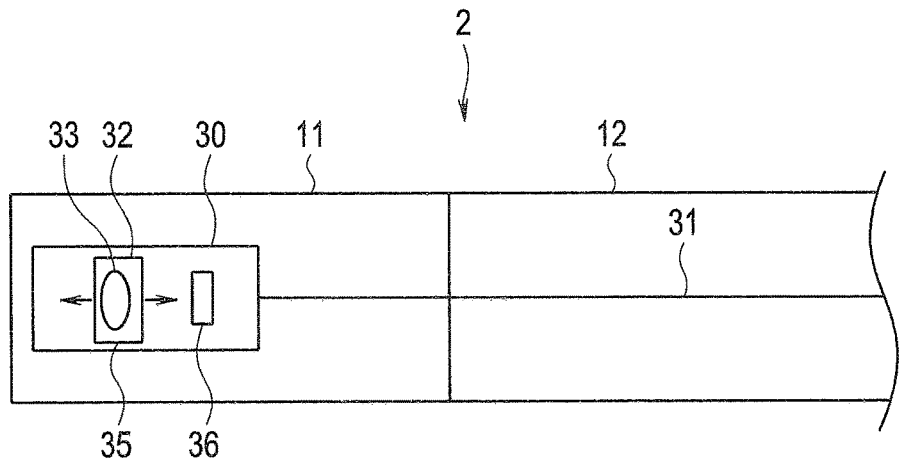
FIG. 2 is a schematic diagram illustrating a distal end part of an insertion portion.
Figure 3:
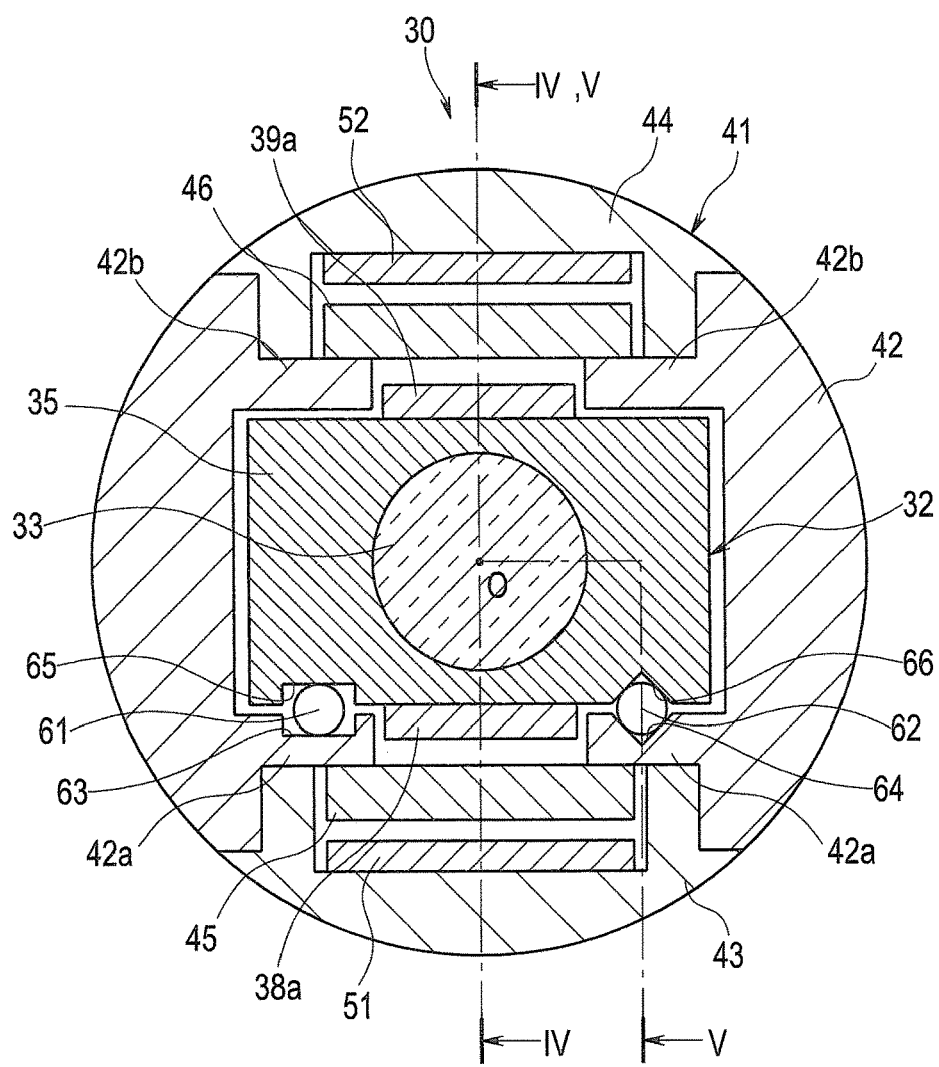
FIG. 3 is a sectional view illustrating a configuration of a moving lens unit inside a fixed barrel.
Figure 4:
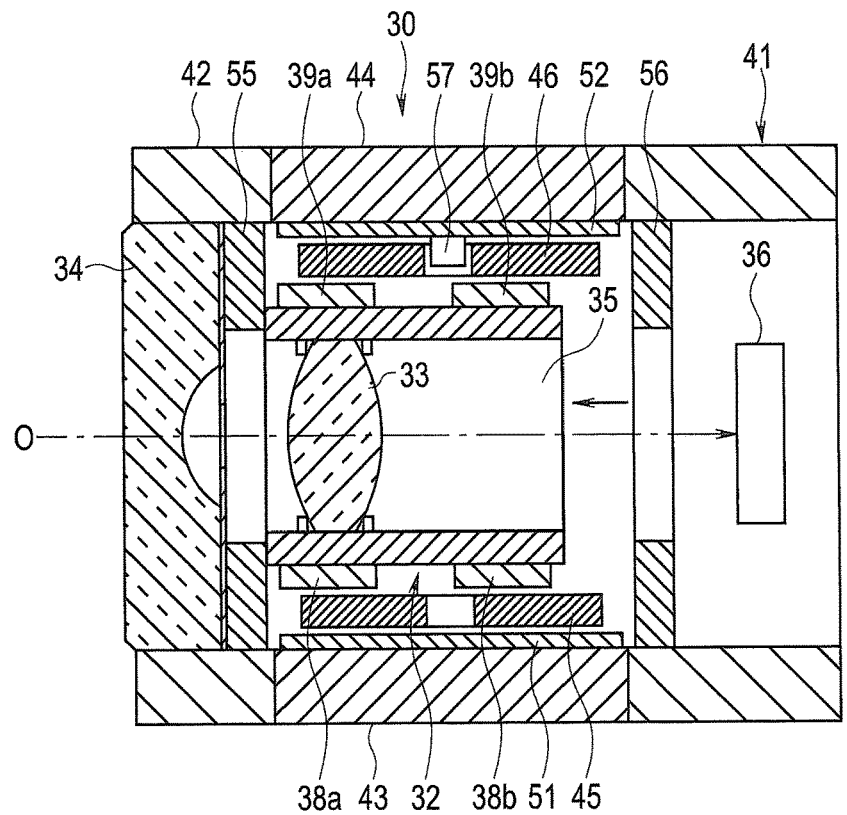
FIG. 4 is a sectional view illustrating the configuration of the moving lens unit inside the fixed barrel along a IV-IV line in FIG. 3.
Figure 5:
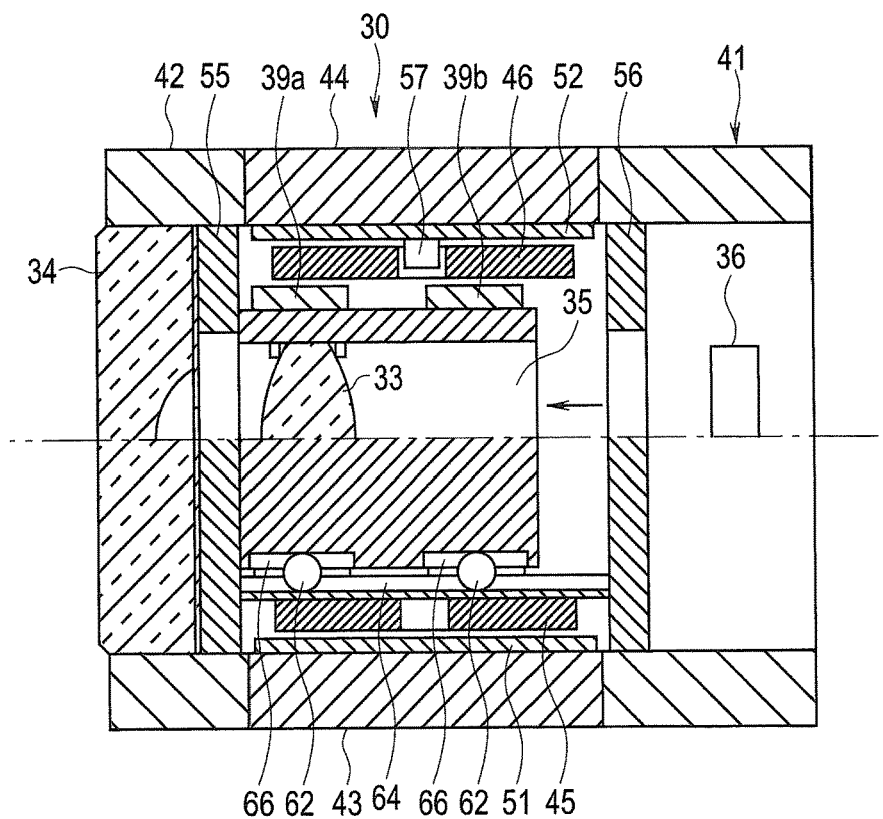
FIG. 5 is a sectional view illustrating the configuration of the moving lens unit inside the fixed barrel along a V-V line in FIG. 3.
Figure 6:
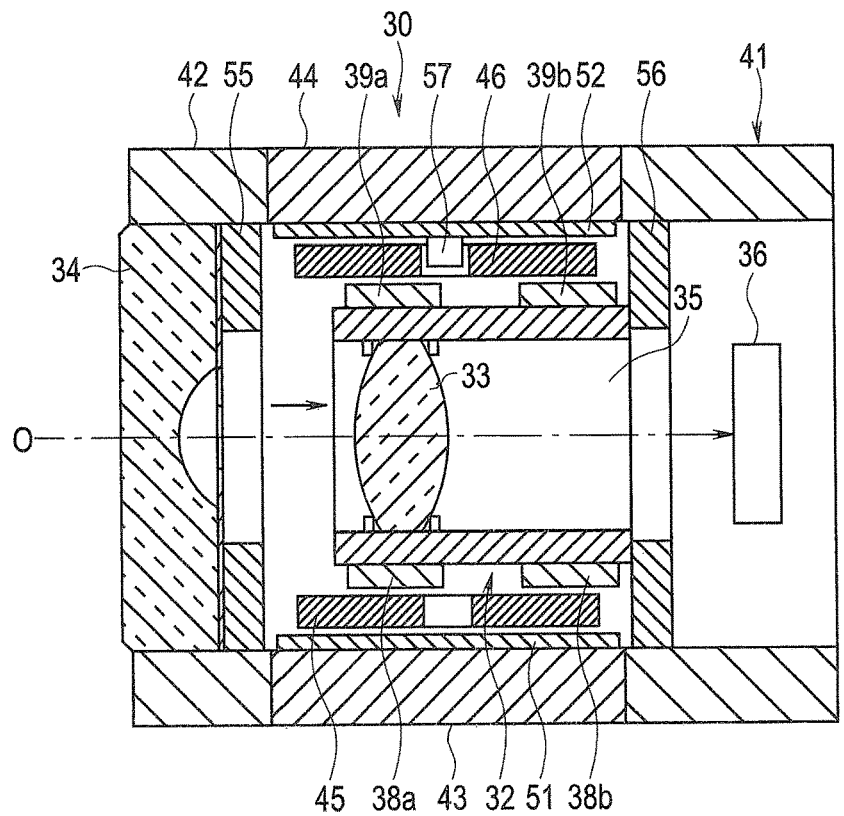
FIG. 6 is a sectional view illustrating a state where the moving lens unit inside the fixed barrel moves to a proximal end side corresponding to the IV-IV line in FIG. 3.
Figure 7:
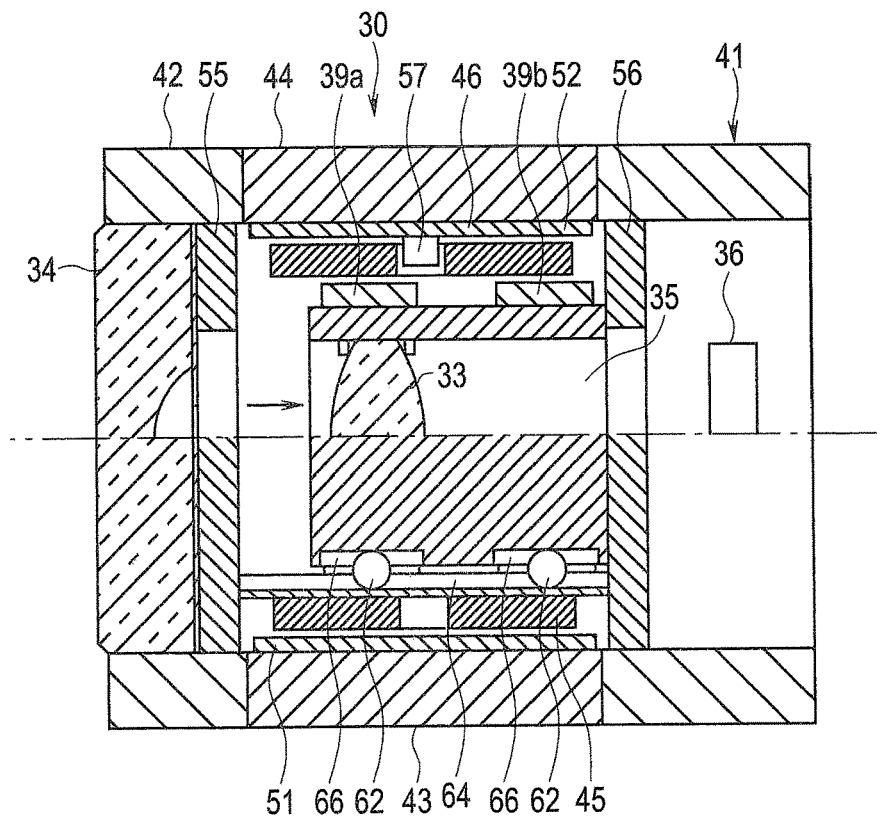
FIG. 7 is a sectional view illustrating a state where the moving lens unit inside the fixed barrel moves to the proximal end side corresponding to the V-V line in FIG. 3.
Figure 8:
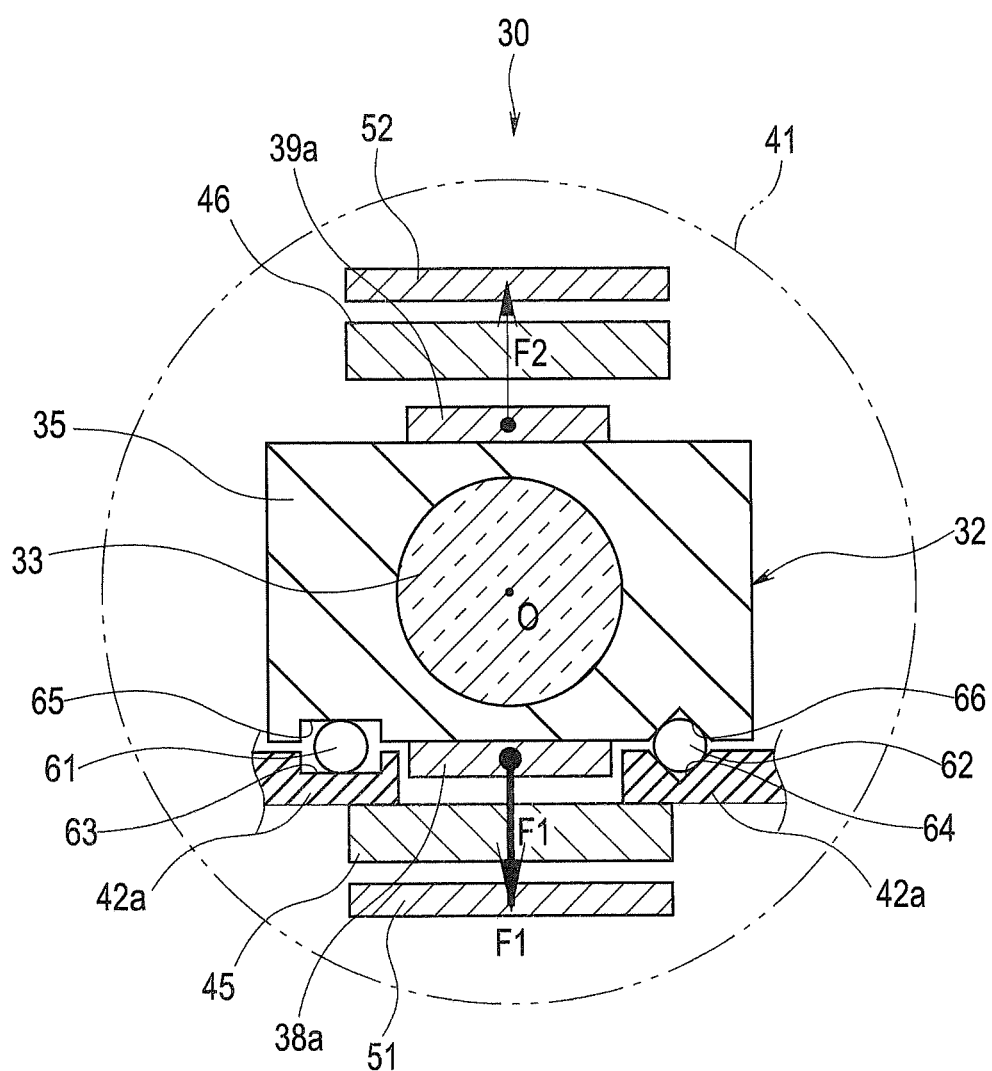
FIG. 8 is a partial sectional view for explaining a state where the moving lens unit is attracted to a ball sliding side.
Figure 9:
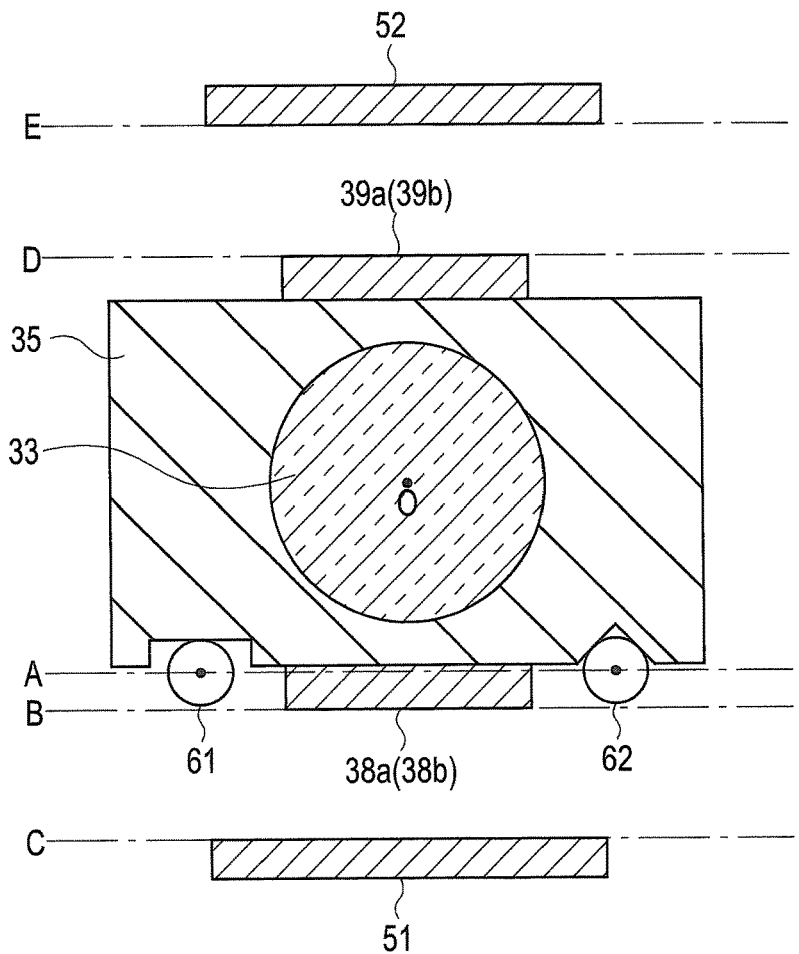
FIG. 9 is a lateral sectional view of the moving lens unit explaining an arranged state of components regarding ball sliding.
Figure 10:
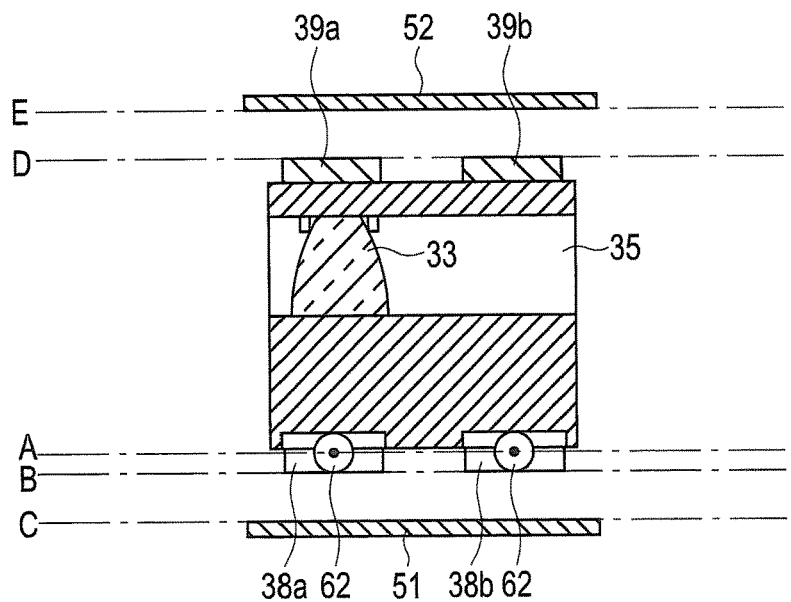
FIG. 10 is a longitudinal sectional view of the moving lens unit explaining the arranged state of the components regarding the ball sliding.
Figure 11:
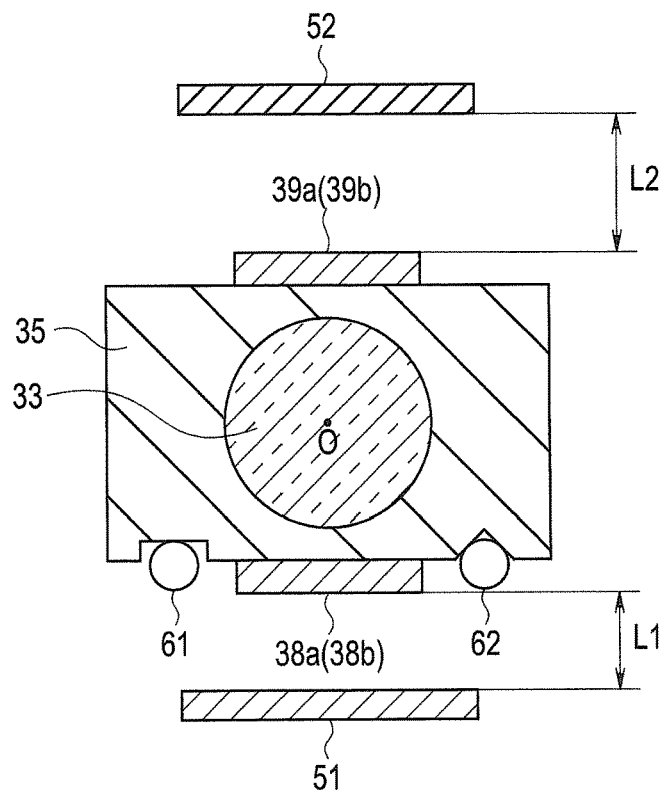
FIG. 11 is a sectional view of the moving lens unit explaining one example of arrangement of a permanent magnet and a ferromagnetic body.
Figure 12:
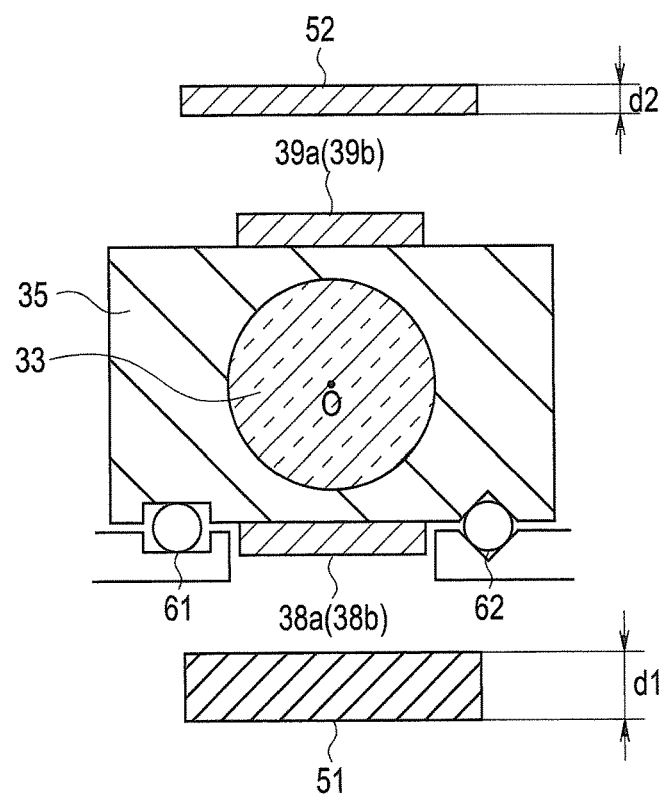
FIG. 12 is a sectional view of the moving lens unit explaining another example of the arrangement of the permanent magnet and the ferromagnetic body.
Figure 13:
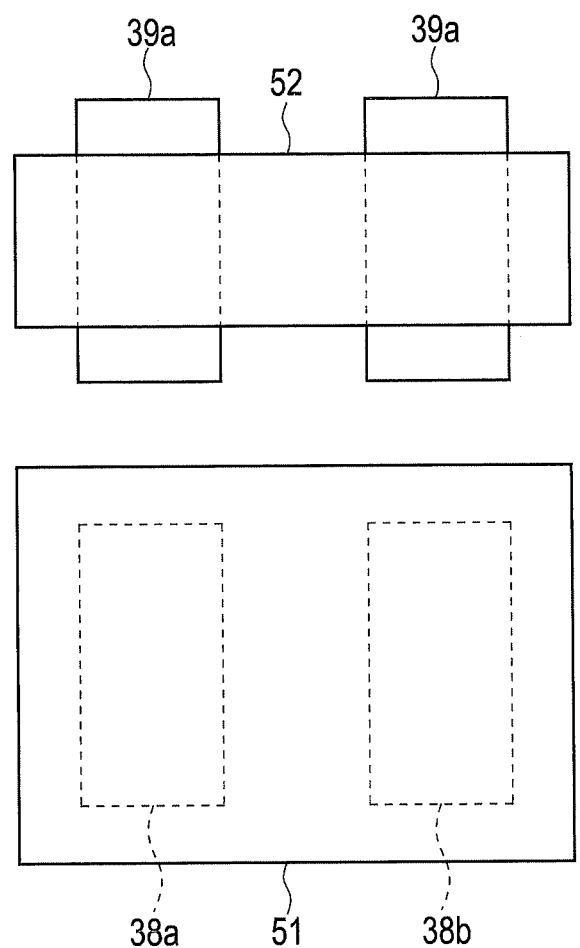
FIG. 13 is a plan view explaining another example of the arrangement of the permanent magnet and the ferromagnetic body.

FIG. 1 is a perspective view illustrating a configuration of an endoscope, FIG. 2 is a schematic diagram illustrating a distal end part of an insertion portion, and FIG. 3 is a sectional view illustrating a configuration of a moving lens unit inside a fixed barrel. FIG. 4 is a sectional view illustrating the configuration of the moving lens unit inside the fixed barrel along a IV-IV line in FIG. 3, FIG. 5 is a sectional view illustrating the configuration of the moving lens unit inside the fixed barrel along a V-V line in FIG. 3, FIG. 6 is a sectional view illustrating a state where the moving lens unit inside the fixed barrel moves to a proximal end side corresponding to the IV-IV line in FIG. 3, and FIG. 7 is a sectional view illustrating a state where the moving lens unit inside the fixed barrel moves to the proximal end side corresponding to the V-V line in FIG. 3. FIG. 8 is a partial sectional view for explaining a state where the moving lens unit is attracted to a ball sliding side, FIG. 9 is a lateral sectional view of the moving lens unit explaining an arranged state of components regarding ball sliding, and FIG. 10 is a longitudinal sectional view of the moving lens unit explaining the arranged state of the components regarding the ball sliding. FIG. 11 is a sectional view of the moving lens unit explaining one example of arrangement of a permanent magnet and a ferromagnetic body, FIG. 12 is a sectional view of the moving lens unit explaining another example of the arrangement of the permanent magnet and the ferromagnetic body, and FIG. 13 is a plan view explaining another example of the arrangement of the permanent magnet and the ferromagnetic body.

Note that in the individual drawings used in following description, a scale is sometimes made different for each component in order to make the individual components into such sizes that the components can be recognized on the drawings. In addition, the present invention is not limited only to quantities of the components, shapes of the components, ratios of the sizes of the components, and relative positional relationships of the individual components described in the drawings.

As illustrated in FIG. 1, an endoscope 1 is configured mainly to include a long insertion portion 2, an operation portion 3 consecutively connected with a proximal end of the insertion portion 2, a light guide connector 4 connected to a light source device not illustrated, and a video connector 5 connected to a video system center not illustrated.

Note that for the endoscope 1, the operation portion 3 and the light guide connector 4 are connected through a flexible cable 6, and the light guide connector 4 and the video connector 5 are connected through a communication cable 7.

To the insertion portion 2, a distal end portion 11 formed of a rigid member formed of mainly stainless steel, a rigid resin or the like, a bending portion 12, and a rigid tube 13 of a metal tube of mainly the stainless steel or the like are consecutively connected in order from a distal end side. The insertion portion 2 is a part to be inserted into a body, and various kinds of cables for communication and drive, and a non-illustrated light guide that transmits illumination light or the like are incorporated inside.

The operation portion 3 includes angle levers 14 and 15 configured to remotely operate the bending portion 12, and various kinds of switches 16 for operating the light source device and the video system center or the like. The angle levers 14 and 15 are bending operation means capable of operating the bending portion 12 of the insertion portion 2 in four up, down, right and left directions. Note that the endoscope 1 of the present embodiment is a rigid endoscope apparatus in which a large portion of the insertion portion 2 other than the bending portion 12 is rigid. Note that the endoscope 1 may be a flexible endoscope apparatus in which the insertion portion 2 is flexible.

Next, based on FIG. 2, an image pickup apparatus 30 which is an optical unit of the present embodiment disposed at the distal end portion 11 of the insertion portion 2 will be described.

As illustrated in FIG. 2, the image pickup apparatus 30 is disposed inside the distal end portion 11, and a composite cable 31 for which the various kinds of cables for the communication and the drive are bound is extended at a rear part. The composite cable 31 is inserted and arranged inside the insertion portion 2, and is electrically connected with the video connector 5 through the flexible cable 6 and the communication cable 7 from the operation portion 3.

In the image pickup apparatus 30, an image pickup device 36 is disposed, and a circuit board not illustrated here, to which the image pickup device 36 is electrically connected, is provided. Note that the image pickup device 36 is an extremely small-sized electronic component, and a plurality of elements configured to output an electric signal according to incident light at predetermined timing are arrayed in a planar light receiving portion.

To the image pickup device 36, a form generally called a CCD (charge coupled device) or a CMOS (complementary metal oxide semiconductor) sensor or the like for example or the other various kinds of forms are applied.

Then, an image pickup signal photoelectrically converted by the image pickup device 36 is generated into a video signal and outputted by the circuit board. In other words, in the present embodiment, an optical image (endoscope image) picked up by the image pickup device 36 is transmitted to the video connector 5 as the video signal. Note that the endoscope image is displayed on a monitor through a video processor not illustrated here, to which the video connector 5 of the endoscope 1 is connected.

In the image pickup apparatus 30, an objective optical system is disposed. Then, the image pickup apparatus 30 is configured such that a moving lens unit 32 including a moving lens frame 35 which is a moving frame that holds a moving lens 33 here of the objective optical system is disposed, and a zoom function or a focus function is provided. Note that the moving lens 33 held by the moving lens frame 35 is not limited to one piece and may be in plurality.

The moving lens unit 32 is, as illustrated in FIG. 3-FIG. 7, disposed so as to freely move back and forth in a direction along an optical axis O which is an optical axis of the objective optical system including the moving lens 33, inside a fixed barrel 41 of the image pickup apparatus 30.

Note that the fixed barrel 41 holds a cover lens 34 (see FIG. 4-FIG. 7) at a distal end, is formed of a non-magnetic body of metal such as non-magnetic stainless steel, aluminum or copper or the rigid resin, and is a member, an external shape of which is cylindrical here.

The fixed barrel 41 includes a main body frame 42 of the non-magnetic body provided with opening portions at upper and lower parts in a view toward a paper surface to be center point symmetrical positions, and two lid frames 43 and 44 of the non-magnetic body that close the opening portions of the main body frame 42 are fitted and fixed with an adhesive material or the like.

At the respective opening portions of the main body frame 42, coils 45 and 46 are disposed. The coils 45 and 46 are fixed to protruding portions 42a and 42b protruding to an inner side of the main body frame 42 by adhesion or the like.

In addition, for the lid frames 43 and 44, magnetic members 51 and 52 which are energizing members (suction members) in a planar shape here, formed of a ferromagnetic body such as iron or nickel are fixed to respective inner surfaces by the adhesion or the like. Note that details of an action by the magnetic members 51 and 52 will be described later.

In the moving lens unit 32, the moving lens frame 35 holds the moving lens 33 which is the objective optical system as described above. The moving lens frame 35 is disposed so as to freely move back and forth inside the fixed barrel 41.

A cross section of the moving lens frame 35 here is rectangular, and for two each of permanent magnets 38a, 38b, 39a and 39b on each of two upper and lower surfaces in the view toward the paper surface, a predetermined magnetization direction is set. In other words, the permanent magnets 38a, 38b, 39a and 39b are disposed at the center point symmetrical positions of the moving lens frame 35.

Note that for the four permanent magnets 38a, 38b, 39a and 39b, the two permanent magnets 38a and 38b on one surface (lower surface) side and the two permanent magnets 39a and 39b on the other surface (upper surface) side are provided in parallel such that SN polarities at front and back are opposite in a longitudinal direction of the moving lens frame 35 along the optical axis O (see FIG. 4-FIG. 7).

Note that the two coils 45 and 46 are wound around an axis orthogonal to the optical axis O, and are electrically connected with an electric cable inside the composite cable 31, and by switching an energizing direction, a direction of electromagnetic force to be generated is switched.

In this way, by the four permanent magnets 38a, 38b, 39a and 39b in total fixed to the two separate surfaces of the moving lens frame 35 and the coils 45 and 46 fixed to the main body frame 42, a voice coil motor (hereinafter, referred to as a VCM) is configured. Therefore, the VCM becomes an actuator as a drive source that makes the moving lens unit 32 move back and forth along the optical axis O.

The moving lens frame 35 is rectilinearly guided when moving back and forth inside the fixed barrel 41 by ball sliding.

More specifically, between the main body frame 42 and the moving lens frame 35, four balls 61 and 62 in total as interposing members which are spherical bodies formed of a metal or ceramic or the like are provided. The balls 61 and 62 are disposed at the front and the back in the longitudinal direction of the moving lens frame 35 along the optical axis O. Note that the balls 61 and 62 are not limited to four pieces and may be two pieces or more.

At the protruding portion 42a provided on the main body frame 42, to which one coil 45 is fixed, two rail-like guide grooves 63 and 64 having a predetermined length along the optical axis O that guide the back and forth movement of the balls 61 and 62 are formed. Note that the cross section of one guide groove 63 is rectangular, and the cross section of the other guide groove 64 is V-shaped.

The two guide grooves 63 and 64 are disposed respectively in right and left directions with the optical axis O as a boundary.

For the moving lens frame 35, on a surface provided with the permanent magnets 38a and 38b, four receiving portions 65 and 66 that are long ball holding grooves in a recessed portion shape configured to house the four balls 61 and 62 are formed. Note that the cross section of the two receiving portions 65 on one side is rectangular, and the cross section of the two receiving portions 66 on the other side is V-shaped.

In other words, on one surface (upper surface here) of the protruding portion 42a of the main body frame 42 and one surface (lower surface here) of the moving lens frame 35 facing each other, the guide grooves 63 and 64 and the receiving portions 65 and 66 where the balls 61 and 62 are arranged are formed respectively.

Note that the guide groove 63 and the receiving portions 65 of the rectangular sectional shape are formed at facing positions, and the guide groove 64 and the receiving portions 66 of the V-shaped sectional shape are formed at the facing positions. In other words, the plurality of receiving portions 65 and 66 are also disposed respectively in the right and left directions with the optical axis O as the boundary.

In this way, the moving lens frame 35 is guided by the ball sliding that the balls 61 and 62 are rotated along the guide groove 63, and is made to move back and forth along the optical axis O inside the fixed barrel 41 by changeover of the energizing direction to the coils 45 and 46 (see FIG. 4-FIG. 7).

During the back and forth movement, the moving lens frame 35 is restricted from moving to the distal end side by a proximal end face and a distal end face of a contact member 55 disposed inside the main body frame 42 of the fixed barrel 41 being in contact (see FIG. 4 and FIG. 5). In addition, the moving lens frame 35 is restricted from moving to the proximal end side by a distal end face and a proximal end face of a contact member 56 disposed inside the main body frame 42 of the fixed barrel 41 being in contact (see FIG. 6 and FIG. 7).

Note that to the fixed barrel 41, a position detection sensor 57 such as a Hall element configured to detect a back and forth moving position of the moving lens frame 35 is disposed (see FIG. 4-FIG. 7). In addition, the permanent magnets 38a, 38b, 39a and 39b may also serve as magnets for position detection.

Here, the moving lens frame 35 is in the state of being attracted to one surface (lower surface) side as a direction side provided with the ball sliding.

More specifically, as illustrated in FIG. 8, at the moving lens frame 35, by magnetism of the permanent magnets 38a (38b) as first magnets disposed on a ball sliding side, first attractive force F1 that attracts the moving lens frame 35 is generated between the magnetic member 51 as a first ferromagnetic body for which the permanent magnets 38a (38b) are disposed at the facing position in vicinity and the permanent magnets 38a (38b).

Further, at the moving lens frame 35, by the magnetism of the permanent magnets 39a (39b) as second magnets disposed on the side separated from the ball sliding, second attractive force F2 that attracts the moving lens frame 35 is generated between the magnetic member 52 as a second ferromagnetic body for which the permanent magnets 39a (39b) are disposed at the facing positions in the vicinity and the permanent magnets 39a (39b).

Then, the first attractive force F1 is set to be larger than the second attractive force F2 (F1>F2), the magnetic first attractive force F1 generated at the moving lens frame 35 is canceled and mitigated by the second attractive force F2, and the state where urging force (F1−F2) that attracts the moving lens frame 35 to the ball sliding side at all times is generated is attained.

In other words, the image pickup apparatus 30 of the present embodiment is adjusted such that an unneeded force component generated by the first attractive force F1 is canceled by the second attractive force F2 in an opposite direction and the optimum urging force to the ball sliding side is generated at the moving lens frame 35 moving back and forth inside the fixed barrel 41.

In order to bring the four balls 61 and 62 into contact with the guide grooves 63 and 64 by equal force by the attractive force to the ball sliding side, the permanent magnets 38a, 38b, 39a and 39b and the magnetic members 51 and 52 here are in the planar shape, and are, as illustrated in FIG. 9 and FIG. 10, provided so as to be parallel to a plane A passing through centers of the four balls 61 and 62.

In other words, facing planes B and C of the permanent magnets 38a and 38b and the magnetic member 51 are parallel to the plane A passing through the centers of the balls 61 and 62, and facing planes D and E of the permanent magnets 39a and 39b and the magnetic member 52 are parallel to the plane A passing through the centers of the balls 61 and 62.

Thus, the first attractive force F1 and the second attractive force F2 become the attractive force in the direction orthogonal to the plane A passing through the centers of the four balls 61 and 62, and the four balls 61 and 62 are brought into contact with the guide grooves 63 and 64 by the equal force. As a result, the moving lens frame 35 inside the fixed barrel 41 can smoothly move back and forth in the direction along the optical axis O without generation of a rotation moment by magnetic force.

Various configurations for making the first attractive force F1 larger than the second attractive force F2 (F1>F2) as described above are conceivable.

As one example, as illustrated in FIG. 11, when a clearance L2 between the permanent magnets 39a and 39b which are the second magnets and the magnetic member 52 which is the second ferromagnetic body is made larger (longer) than a clearance L1 between the permanent magnets 38a and 38b which are the first magnets and the magnetic member 51 which is the first ferromagnetic body (L1<L2), the first attractive force F1 can be made larger than the second attractive force F2 (F1>F2).

As another example, as illustrated in FIG. 12, when a thickness d1 of the magnetic member 51 which is the first ferromagnetic body is made larger (thicker) than a thickness d2 of the magnetic member 52 which is the second ferromagnetic body (d1>d2), the first attractive force F1 can be made larger than the second attractive force F2 (F1>F2).

Further, as another example, as illustrated in FIG. 13, when a surface area of the magnetic member 51 which is the first ferromagnetic body facing the permanent magnets 38a and 38b which are the first magnets is made larger (wider) than the surface area of the magnetic member 52 which is the second ferromagnetic body facing the permanent magnets 39a and 39b which are the second magnets, the first attractive force F1 can be made larger than the second attractive force F2 (F1>F2).

Note that though not illustrated here, the surface area of the permanent magnets 38a and 38b which are the first magnets facing the magnetic member 51 which is the first ferromagnetic body may be made larger than the surface area of the permanent magnets 39a and 39b which are the second magnets facing the magnetic member 52 which is the second ferromagnetic body.

As described above, the image pickup apparatus 30 which is the optical unit of the present embodiment is configured to adjust the force toward the ball sliding by generating the magnetic force in two opposite directions orthogonal to the optical axis O at the moving lens frame 35 that moves back and forth for the zoom function or the focus function, without being enlarged. By such a configuration, in the image pickup apparatus 30, setting for smoothly driving the moving lens frame 35 in the direction along the optical axis O without loss even with small driving force of the VCM which is the small-sized actuator can be easily performed.

Therefore, the image pickup apparatus 30 which is the optical unit can smoothly slide the moving lens frame 35 as the small-sized configuration without being enlarged. Note that in the present embodiment, since the image pickup apparatus 30 is the optical unit disposed in the endoscope 1, the first attractive force F1 and the second attractive force F2 are set so as to generate the optimum urging force to the ball sliding side at the moving lens frame 35 in any posture.

First Modification

Figure 14:
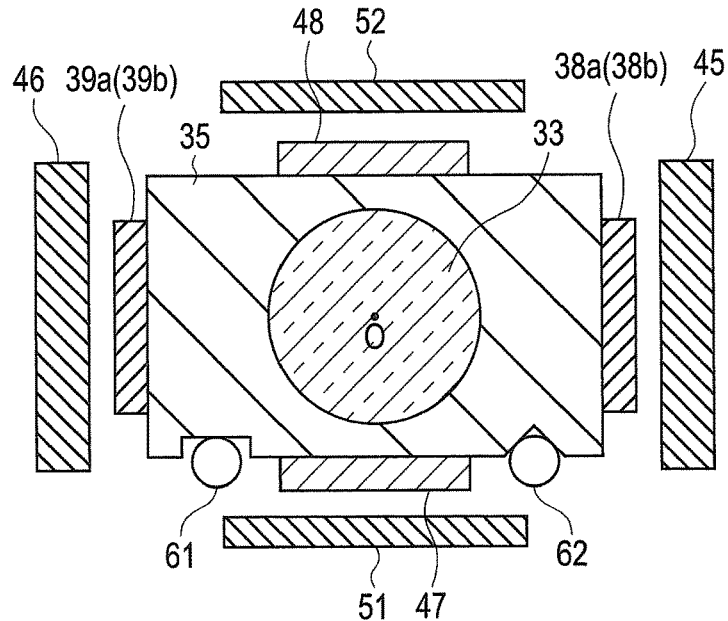
FIG. 14 is a sectional view illustrating a configuration of a moving lens unit of a first modification.

FIG. 14 is a sectional view illustrating a configuration of a moving lens unit of the first modification.

As illustrated in FIG. 14, the image pickup apparatus 30 which is the optical unit may be configured such that the permanent magnets 38a, 38b, 39a and 39b are provided on both side faces of the moving lens frame 35 and back and forth driving force is generated by the coils 45 and 46 disposed on the sides to face the permanent magnets 38a, 38b, 39a and 39b.

In such a configuration, permanent magnets 47 and 48 which are the first magnet and the second magnet are disposed separately on the upper and lower surfaces of the moving lens frame 35, and the state where the moving lens frame 35 is attracted and urged to the ball sliding side at all times is attained.

In other words, the image pickup apparatus 30 which is the optical unit of the present modification is configured such that the permanent magnets 38*a*, 38*b*, 39*a* and 39*b* for the drive and the permanent magnets 47 and 48 for urging the moving lens frame 35 to the ball sliding side are different. Note that the permanent magnets 47 and 48 may also serve as the magnets for the position detection.

Second Modification

Figure 15:
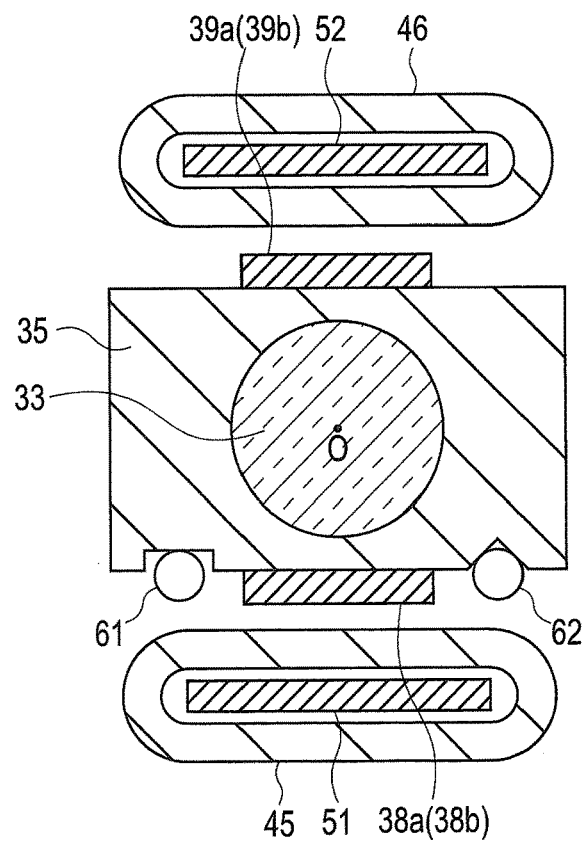
FIG. 15 is a sectional view illustrating a configuration of a moving lens unit of a second modification.

FIG. 15 is a sectional view illustrating a configuration of a moving lens unit of the second modification.

As illustrated in FIG. 15, the coils 45 and 46 disposed in the image pickup apparatus 30 which is the optical unit may be wound around an axis parallel to the optical axis O and the magnetic members 51 and 52 may be disposed inside the coils 45 and 46. Note that the magnetic members 51 and 52 may not always be disposed inside the coils 45 and 46.

Third Modification

Figure 16:
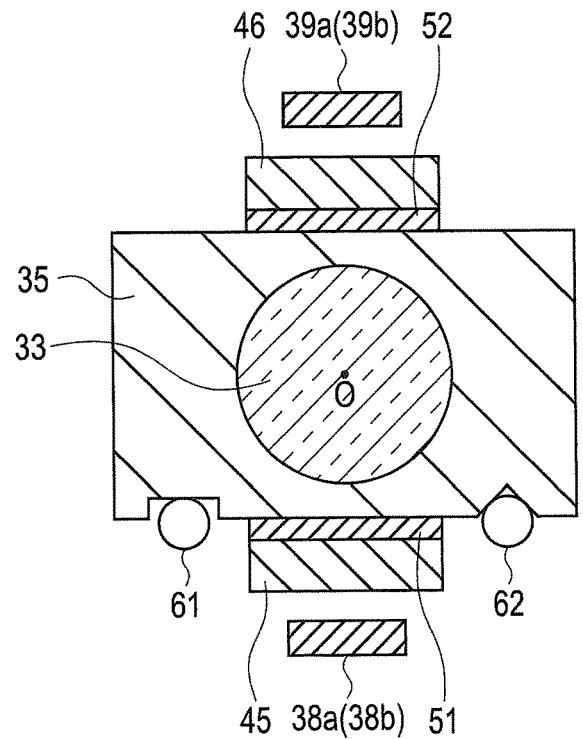
FIG. 16 is a sectional view illustrating a configuration of a moving lens unit of a third modification.

FIG. 16 is a sectional view illustrating a configuration of a moving lens unit of the third modification.

As illustrated in FIG. 16, the image pickup apparatus 30 which is the optical unit may be configured such that the magnetic members 51 and 52 and the coils 45 and 46 are stacked and disposed on the upper and lower surfaces of the moving lens frame 35, and the permanent magnets 38*a*, 38*b*, 39*a* and 39*b* are provided on the side of the fixed barrel 41 not illustrated here.

Fourth Modification

Figure 17:
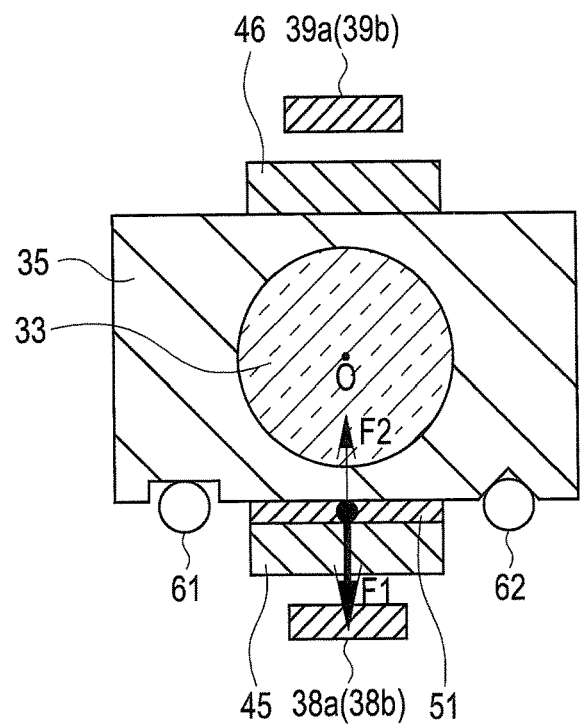
FIG. 17 is a sectional view illustrating a configuration of a moving lens unit of a fourth modification.

FIG. 17 is a sectional view illustrating a configuration of a moving lens unit of the fourth modification.

As illustrated in FIG. 17, for the image pickup apparatus 30 which is the optical unit, the third modification is modified further, and the image pickup apparatus 30 may be configured such that the magnetic member 51 is provided only on the lower surface of the moving lens frame 35 and the coil 45 is stacked and disposed on the magnetic member 51.

In the image pickup apparatus 30 configured in this way, since the two separate kinds of the attractive force F1 and F2 generated among the permanent magnets 38*a*, 38*b*, 39*a* and 39*b* acting on one magnetic member 51 cancel each other and the attractive force F1 is mitigated, the state where the urging force (F1−F2) that attracts the moving lens frame 35 to the ball sliding side at all times is generated can be attained.

The invention described in the above embodiment is not limited to the above-described embodiment and can be variously modified without departing from the scope in an implementation phase in addition. Further, the above-described embodiment includes the inventions in various stages, and various inventions can be extracted by appropriate combinations in a plurality of disclosed constituent elements.

For example, even when some constituent elements are deleted from the entire constituent elements indicated in the embodiment, in a case where the described problem can be solved and the described effect can be obtained, the configuration from which the constituent elements are deleted can be extracted as the invention.

What is claimed is:

1. An optical unit comprising:
a moving frame disposed so as to freely move back and forth inside a fixed barrel, the moving frame being configured to hold a moving lens;
an actuator configured to drive the moving frame along an optical axis of the moving lens;
a plurality of spherical bodies disposed on a first surface of the moving frame, the plurality of spherical bodies being configured to make the moving frame slidable with respect to the fixed barrel in a direction along the optical axis;
a plurality of guide grooves formed on a second surface of the fixed barrel, the second surface facing the first surface of the moving frame, the plurality of guide grooves being configured to guide sliding of the plurality of spherical bodies along the optical axis;
a plurality of magnets disposed on the moving frame at point symmetrical positions around the optical axis, the plurality of magnets including a first magnet disposed on a first side of the optical axis having the plurality of spherical bodies and a second magnet disposed on a second side of the first magnet, the second side being opposite to the first side across the optical axis; and
a first magnetic member provided on the fixed barrel at a first position facing the first magnet; and
a second magnetic member provided on the fixed barrel at a second position facing the second magnet,
wherein a first attractive force generated between the first magnetic member and the first magnet is greater than a second attractive force generated between the second magnetic member and the second magnet.

2. The optical unit according to claim 1, wherein
the first magnet has a first planar shape disposed in a first plane and the first magnetic member has a second planar shape disposed in a second plane, the first magnet and the first magnetic member are arranged facing each other;
the second magnet has a third planar shape disposed in a third plane and the second magnetic member has a fourth planar shape disposed in a fourth plane, the second magnet and the second magnetic member are arranged facing with each other; and
the first, second, third and fourth planes are parallel to a fifth plane passing through centers of the plurality of spherical bodies.

3. The optical unit according to claim 2, wherein,
the first magnet is disposed on the first side with respect to the optical axis at a first distance from the first magnetic member disposed at the first position facing the first magnet,
the second magnet is disposed on the second side with respect to the optical axis at a second distance from the second magnetic member disposed at the second position facing the second magnet, and
the first distance is greater than the second distance.

4. The optical unit according to claim 2, wherein,
the first magnet has a first thickness in a first radial direction from the optical axis,
the second magnet has a second thickness in a second radial direction from the optical axis, the second radial direction being opposite to the first radial direction, and
the first thickness is greater than the second thickness.

5. The optical unit according to claim 2, wherein,
the first magnet having a first surface area in the first plane,
the second magnet having a second surface area in the third plane, and
the first surface area is greater than the second surface area.

6. The optical unit according to claim 2, wherein the moving frame comprises a plurality of holding grooves formed on the first surface of the moving frame, the plurality of holding grooves respectively corresponding to the plurality of guide grooves, the plurality of spherical bodies being held in the plurality of guide grooves and the plurality of holding grooves.

7. The optical unit according to claim 1, wherein the plurality of guide grooves are respectively arranged with the optical axis as a boundary.

8. The optical unit according to claim 1, wherein the actuator is a voice coil motor including the plurality of magnets and a plurality of coils.

9. The optical unit according to claim 1, further comprising an image pickup device provided in the fixed barrel, the image pickup device being disposed proximally relative to the moving frame.

10. An endoscope comprising:
an insertion portion; and
the optical unit according to claim 1 disposed at a distal end portion of the insertion portion.

11. An optical unit comprising:
a moving frame disposed so as to freely move back and forth inside a fixed barrel, the moving frame being configured to hold a moving lens;
an actuator configured to drive the moving frame along an optical axis of the moving lens;
a plurality of spherical bodies disposed on a first surface of the moving frame, the plurality of spherical bodies being configured to make the moving frame slidable with respect to the fixed barrel in a direction along the optical axis;
a plurality of guide grooves formed on a second surface of the fixed barrel, the second surface facing the first surface of the moving frame, the plurality of guide grooves being configured to guide sliding of the plurality of spherical bodies along the optical axis;
a first magnet disposed on the moving frame so as to generate a first magnetic force in a first direction which is orthogonal to the optical axis, the first direction being toward a first side of the optical axis having the plurality of spherical bodies;
a second magnet disposed on the moving frame so as to generate a second magnetic force in a second direction which is orthogonal to the optical axis, the second direction being toward a second side of the optical axis, the second side being opposite to the first side across the optical axis;
a first magnetic member provided on the fixed barrel at a first position on the first side, the first magnetic member facing the first magnet; and
a second magnetic member provided on the fixed barrel at a second position on the second side, the second magnetic member facing the second magnet,
wherein a first attractive force generated between the first magnetic member and the first magnet is greater than a second attractive force generated between the second magnetic member and the second magnet such that the plurality of spherical bodies are biased into contact with the plurality of guide grooves.

12. The optical unit according to claim 11, wherein
the first magnet has a first planar shape disposed in a first plane and the first magnetic member has a second planar shape disposed in a second plane, the first magnet and the first magnetic member are arranged facing each other;
the second magnet has a third planar shape disposed in a third plane and the second magnetic member has a fourth planar shape disposed in a fourth plane, the second magnet and the second magnetic member are arranged facing with each other; and
the first, second, third and fourth planes are parallel to a fifth plane passing through centers of the plurality of spherical bodies.

13. The optical unit according to claim 12, wherein,
the first magnet is disposed on the first side with respect to the optical axis at a first distance from the first magnetic member disposed at the first position facing the first magnet, and
the second magnet is disposed on the second side with respect to the optical axis at a second distance from the second magnetic member disposed at the second position facing the second magnet, and
the first distance is greater than the second distance.

14. The optical unit according to claim 12, wherein,
the first magnet has a first thickness in a first radial direction from the optical axis,
the second magnet has a second thickness in a second radial direction from the optical axis, the second radial direction being opposite to the first radial direction, and
the first thickness is greater than the second thickness.

15. The optical unit according to claim 12, wherein,
the first magnet having a first surface area in the first plane,
the second magnet having a second surface area in the third plane, and
the first surface area is greater than the second surface area.

16. The optical unit according to claim 11, wherein the plurality of guide grooves are respectively arranged with the optical axis as a boundary.

17. The optical unit according to claim 11, wherein the actuator is a voice coil motor including the plurality of magnets and a plurality of coils.

18. The optical unit according to claim 11, further comprising an image pickup device provided in the fixed barrel, the image pickup device being disposed proximally relative to the moving frame.

19. An endoscope comprising:
an insertion portion; and
the optical unit according to claim 11 disposed at a distal end portion of the insertion portion.

20. The optical unit according to claim 11, wherein the moving frame comprises a plurality of holding grooves formed on the first surface of the moving frame, the plurality of holding grooves respectively corresponding to the plurality of guide grooves, the plurality of spherical bodies being held in the plurality of guide grooves and the plurality of holding grooves.

* * * * *